United States Patent
Adebayo-Ige et al.

(10) Patent No.: US 11,673,848 B2
(45) Date of Patent: Jun. 13, 2023

(54) XYLENE SEPARATION PROCESSES USING A MEMBRANE SEPARATOR

(71) Applicant: ExxonMobil Chemical Patents Inc., Baytown, TX (US)

(72) Inventors: Oluwagbogo Adebayo-Ige, Houston, TX (US); Robert G. Tinger, Friendswood, TX (US); Todd E. Detjen, Bellaire, TX (US); Bhupender S. Minhas, Bridgewater, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/795,901

(22) PCT Filed: Jan. 11, 2021

(86) PCT No.: PCT/US2021/012908
§ 371 (c)(1),
(2) Date: Jul. 28, 2022

(87) PCT Pub. No.: WO2021/173238
PCT Pub. Date: Sep. 2, 2021

(65) Prior Publication Data
US 2023/0089144 A1    Mar. 23, 2023

Related U.S. Application Data

(60) Provisional application No. 62/982,425, filed on Feb. 27, 2020.

(30) Foreign Application Priority Data

Apr. 21, 2020 (EP) ..................... 20170579

(51) Int. Cl.
*C07C 7/12* (2006.01)
*C07C 15/08* (2006.01)
(Continued)

(52) U.S. Cl.
CPC ............ *C07C 7/12* (2013.01); *B01D 15/1821* (2013.01); *B01D 61/38* (2013.01); *B01D 69/142* (2013.01); *C07C 15/08* (2013.01)

(58) Field of Classification Search
None
See application file for complete search history.

(56) References Cited

U.S. PATENT DOCUMENTS

| | | |
|---|---|---|
| 3,201,491 A | 8/1965 | Stine et al. |
| 3,626,020 A | 12/1971 | Neuzil |

(Continued)

FOREIGN PATENT DOCUMENTS

| | | |
|---|---|---|
| WO | 2016/133589 A1 | 8/2016 |
| WO | 2017/048378 A1 | 3/2017 |
| WO | 2021/173238 A1 | 9/2021 |

OTHER PUBLICATIONS

Extended European Search Report received for European Patent Application No. 20170579.5 dated Oct. 5, 2020, 6 Pages.

(Continued)

*Primary Examiner* — Tam M Nguyen

(57) ABSTRACT

A process and system for separating paraxylene from a mixture of paraxylene, metaxylene, orthoxylene, and ethylbenzene in a simulated moving bed apparatus using a membrane to separate non-aromatics from a desorbent stream. The lower nonaromatics content in the desorbent improves paraxylene product purity, increases paraxylene production at the same desorbent rate, reduces the desorbent rate, and/or reduces energy consumption in the product tower.

25 Claims, 3 Drawing Sheets

(51) Int. Cl.
  *B01D 69/14* (2006.01)
  *B01D 61/38* (2006.01)
  *B01D 15/18* (2006.01)

(56) References Cited

U.S. PATENT DOCUMENTS

| | | |
|---|---|---|
| 3,761,533 A | 9/1973 | Mori et al. |
| 3,878,127 A | 4/1975 | Rosback |
| 3,943,182 A | 3/1976 | Neuzil et al. |
| 4,029,717 A | 6/1977 | Healy et al. |
| 4,079,094 A | 3/1978 | Rosback et al. |
| 4,088,706 A | 5/1978 | Kaeding |
| 4,108,915 A | 8/1978 | Rosback et al. |
| 4,571,444 A | 2/1986 | Black et al. |
| 4,613,725 A | 9/1986 | Barthomeuf |
| 4,853,202 A | 8/1989 | Kuznicki |
| 5,001,591 A | 3/1991 | Nakashima |
| 5,011,591 A | 4/1991 | Kuznicki |
| 5,244,650 A | 9/1993 | Kuznicki et al. |
| 5,365,004 A | 11/1994 | Beck et al. |
| 5,453,560 A | 9/1995 | Kulprathipanja |
| 5,648,508 A | 7/1997 | Yaghi |
| 6,180,008 B1 | 1/2001 | White |
| 6,187,987 B1 | 2/2001 | Chin et al. |
| 6,369,287 B1 | 4/2002 | Magne-drisch et al. |
| 7,642,393 B2 | 1/2010 | Wang et al. |
| 7,662,746 B2 | 2/2010 | Yaghi et al. |
| 8,283,274 B2 | 10/2012 | Cheng et al. |
| 8,529,757 B2 | 9/2013 | Go et al. |
| 8,704,031 B2 | 4/2014 | Kulprathipanja et al. |
| 9,102,609 B2 | 8/2015 | Yaghi et al. |
| 10,392,324 B2 | 8/2019 | Weber et al. |
| 2005/0038308 A1* | 2/2005 | Wolff .................. C07C 7/12 |
| | | 585/805 |
| 2005/0171395 A1* | 8/2005 | Huff .................. C07C 7/144 |
| | | 585/819 |
| 2009/0149686 A1* | 6/2009 | Leflaive .............. C07C 7/144 |
| | | 585/478 |
| 2009/0305040 A1 | 12/2009 | Schubert et al. |
| 2015/0376088 A1* | 12/2015 | Molinier ............. C07C 7/13 |
| | | 585/314 |
| 2016/0272558 A1* | 9/2016 | Bender ............. C07C 5/2775 |
| 2016/0318827 A1* | 11/2016 | Tinger ............. C07C 5/2729 |
| 2017/0210682 A1* | 7/2017 | Dreux .............. C07C 5/2737 |
| 2018/0002252 A1 | 1/2018 | Salciccioli et al. |
| 2018/0002253 A1* | 1/2018 | Dorsi .................. C07C 7/12 |
| 2018/0009729 A1 | 1/2018 | Ou et al. |
| 2019/0184311 A1 | 6/2019 | Weber et al. |
| 2020/0002252 A1* | 1/2020 | Prevost .............. C07C 7/005 |
| 2021/0261483 A1* | 8/2021 | Prevost ............. B01D 3/143 |

OTHER PUBLICATIONS

Alaerts, L. et al., (2008) "Activation or the metal-organic framework MIL-47 for selective adsorption of xylenes and other difunctionalized aromatics", Physical Chemistry Chemical Physics, vol. 10, No. 20, pp. 2979-2985.
International Preliminary Report on Patentability received for PCT Application No. PCT/US2021/012908, dated Sep. 9, 2022, 9 Pages.
International Search Report and Written Opinion received for PCT Application No. PCT/US2021/012908, dated Mar. 30, 2021, 13 Pages.
Zhang, F. et al., (2015) "Selective Separation of Toluene/n-Heptane by Supported Ionic Liquid Membranes with [Bmim] [BF4]", Chemical Engineering & Technology, vol. 38, No. 2, pp. 355-361.

\* cited by examiner

XYLENE SEPARATION PROCESSES USING A MEMBRANE SEPARATOR

CROSS-REFERENCE TO RELATED APPLICATIONS

This application is a US national phase application of PCT Application Serial No. PCT/US2021/012908 having a filing date of Jan. 11, 2021, which claims priority to and the benefit of U.S. Provisional Application No. 62/982,425 having a filing date of Feb. 27, 2020 and EP Application No. 20170579.5, filed Apr. 21, 2020, the disclosures of all of which are incorporated herein by reference in their entireties.

FIELD

This disclosure relates to a process for separating paraxylene from a mixture comprising $C_8$ aromatics by means of a simulated moving bed adsorption apparatus.

BACKGROUND

Of the three xylene isomers, paraxylene is the most commercially valuable. Due to the similarity of their boiling points, adsorption, using an adsorbent solid which preferentially adsorbs paraxylene over metaxylene and orthoxylene in a simulated moving bed (SMB) apparatus, is a common method for separating paraxylene from the other xylene isomers. Commercial embodiments of an SMB are known from, for example, U.S. Pat. Nos. 3,201,491; 3,761,533; 4,029,717; and 8,529,757.

In an SMB, the locations of liquid input and output are moved by a fluid directing device or devices. This fluid directing device may comprise one or more rotary valves, as well as various control and accessory means, such as inlet lines, outlets lines, and valves associated therewith. The fluid directing device(s) works in conjunction with conduits connected to adsorbent beds. The fluid directing device accomplishes moving the input and output locations by directing the liquid introduction or withdrawal lines to specific conduits in fluid communication with particular adsorbent beds.

Commercial SMB units can have multiple adsorbent beds and respective conduits individually connected to a bed and providing fluid communication with the fluid directing device. The conduits of the adsorption apparatus may function, over time, as at least two liquid input lines (e.g., a feed input line and a desorbent input line) and two liquid output lines (e.g., an extract withdrawal line and a raffinate withdrawal line). The flow rate of streams into and out of the simulated moving bed can be held constant during the step time, and may be modulated as in a PowerFeed process to enhance SMB separation efficiencies, as disclosed in U.S. Patent Document No. 2018-0009729 A1, for example.

Commercial SMB systems also generally include one or more distillation towers and attendant pumps and conduits, which may be utilized to purify the liquid withdrawal streams taken from adsorbent beds. High C8 non-aromatics content in the desorbent can accumulate over time, especially for toluene desorbent. As the non-aromatics accumulate, the amount of this contaminant in the paraxylene product will increase. Often, a portion of the toluene desorbent is purged from the system and replaced with fresh toluene makeup to manage the accumulation of non-aromatic contaminants in the SMB system. However, the practice of desorbent purge and make-up is inefficient, resulting in excessive energy consumption and/or reduced throughputs. What is needed is a way to remove the non-aromatics, and/or improve the energy efficiency of the SMB unit.

The separation of non-aromatics from aromatics using a membrane has been proposed in U.S. Pat. Nos. 4,571,444; 6,187,987; 6,180,008; and Zhang, Fan, "Selective Separation of Toluene/n-Heptane by Supported Ionic Liquid Membranes with [Bmim][BF4]," Chem. Eng. Technol. 2015, 38, No. 2, 355-361. Additional references for citation in an Information Disclosure Statement include U.S. Pat. No. 10,392,324; U.S. 2019-0184311 A1; and WO 2016/133589 A1.

SUMMARY

A process and system are disclosed herein for separating paraxylene (PX) from a mixture of PX, metaxylene (MX), orthoxylene (OX), and ethylbenzene (EB) in a simulated moving bed adsorption apparatus (SMB) using a membrane to separate non-aromatics from a desorbent stream. We have found that processing the desorbent stream or part of it (sidestream) with the membrane separator can result in less toluene purge, which can be matched by toluene in the feed mixture and/or a smaller sized toluene makeup stream. The lower nonaromatics content in the desorbent in turn improves PX product purity, increases PX production at the same desorbent rate, reduces the desorbent rate necessary to maintain the same PX production, and/or reduces energy consumption in the distillation towers downstream of the SMB.

Embodiments disclosed herein provide a process for separating PX from a mixture of PX, MX, OX, and EB, comprising the steps of: (i) processing a feed stream, comprising the mixture, and a desorbent stream, comprising desorbent, in an SMB to produce an extract stream comprising desorbent enriched in PX and a raffinate stream comprising desorbent lean in PX; (ii) fractionating the extract stream to produce a first desorbent-rich stream and a PX-rich stream; (iii) fractionating the raffinate stream to produce a second desorbent-rich stream and a mixed-C8-aromatic-rich stream; (iv) introducing a supply stream comprising at least a portion of one or both of the first desorbent-rich stream, the second desorbent-rich stream, or a combination thereof to a membrane separator to produce a permeate stream and a retentate stream, wherein the retentate stream is rich in non-aromatics relative to the permeate stream; (v) supplying the permeate stream and any remaining portion(s) of the first desorbent-rich stream, the second desorbent-rich stream, or the combination thereof, to the desorbent stream to the simulated moving bed adsorption apparatus; and (vi) purging the retentate stream from the process.

Embodiments disclosed herein also include a system for separating PX from a mixture of PX, MX, OX, and EB, comprising: (i) a simulated moving bed adsorption apparatus to process a feed stream comprising the mixture and a desorbent stream comprising desorbent to produce an extract stream comprising desorbent enriched in PX and a raffinate stream comprising desorbent lean in PX; (ii) an extract fractionation tower to fractionate the extract stream to produce a first desorbent-rich stream and a PX-rich product stream; (iii) a raffinate fractionation tower to fractionate the raffinate stream to produce a second desorbent-rich stream and a mixed-C8-aromatic-rich product stream; (iv) a membrane separator to produce a permeate stream and a retentate stream, wherein the retentate stream is rich in non-aromatics relative to the permeate stream; (v) a supply line to supply a supply stream comprising at least a portion of one or both of the first desorbent-rich stream, the second desorbent-rich stream, or a combination thereof, to the membrane separator; (vi) a return line to return the permeate stream and any remaining portion(s) of the first desorbent-rich stream, the second desorbent-rich stream, or the combination thereof, to the desorbent stream to the SMB; and (vii) a purge line to purge the retentate stream from the system.

These and other objects, features, and advantages will become apparent in the following detailed description, drawings, specific embodiments, experiments, and accompanying claims.

DETAILED DESCRIPTION

Figure 1:
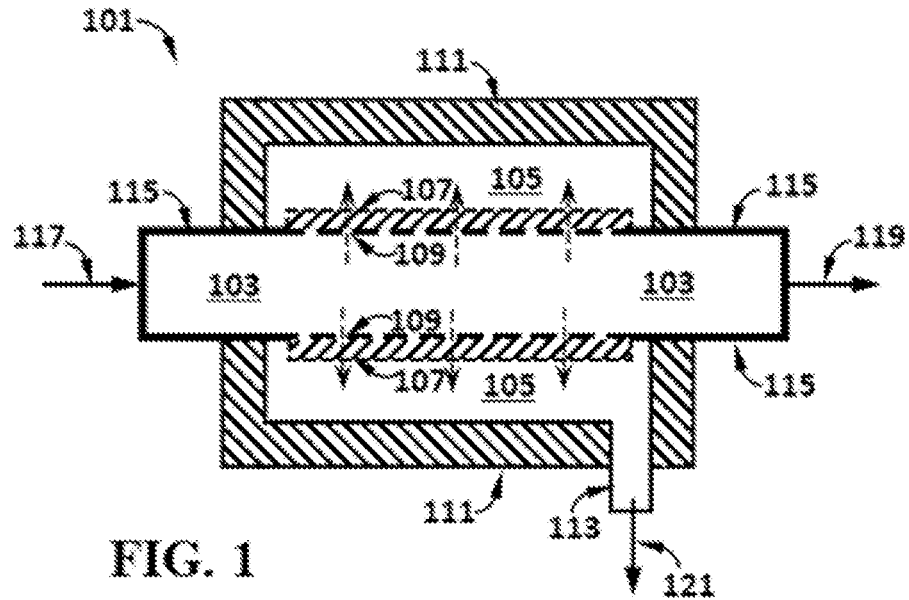
FIG. 1 is a schematic diagram illustrating the structure and operation of a membrane separator useful in embodiments of the processes of this disclosure.

Embodiments disclosed herein utilize a membrane separator on a toluene recycle stream to effectively separate non-aromatics from the process or system.

Definitions

Various terms used in this description will be understood in the context of this description. A further explanation of certain terms used herein is provided below.

The term "$C_n$" hydrocarbon wherein n is a positive integer, means a hydrocarbon having n number of carbon atom(s) per molecule. The terms "$C_{n+}$," hydrocarbon and "$C_{n-}$" hydrocarbon, wherein n is a positive integer, mean a hydrocarbon having at least n number of carbon atom(s) per molecule or no more than n number of carbon atom(s) per molecule, respectively. The term "aromatics" means hydrocarbon molecules containing at least one aromatic core. The term "hydrocarbon" encompasses mixtures of hydrocarbon, including those having different values of n. $C_8$ aromatics are aromatic compounds having 8 carbon atoms. Examples of $C_8$ aromatics include PX, MX, OX, and ethylbenzene.

Equilibrium xylene is a mixture of $C_8$ aromatics having a thermodynamic equilibrium concentration of the various $C_8$ aromatic compounds. A non-selective process for producing xylenes may involve reacting reactants over a non-selective catalyst. Equilibrium xylene may be, for example, in a xylene isomerization process, a transalkylation process, or a reforming process. Equilibrium xylene may also be produced by other processes. Equilibrium xylene may comprise, for example, about 24 percent PX, based on the total quantity of the xylenes.

Enhanced PX is a mixture of $C_8$ aromatics having a greater concentration of PX than equilibrium xylene. Enhanced PX may be produced in a selective process for producing xylenes. A selective process for producing xylenes may involve reacting reactants over a selective catalyst. Enhanced PX may be produced, for example, by a selective toluene disproportionation process or a selective toluene alkylation process Enhanced PX may also be produced by other processes Enhanced PX may have a concentration of, for example, at least 75% PX, based on the total quantity of $C_8$ aromatics.

A non-selective process for producing xylenes is a process which produces equilibrium xylenes. A non-selective process for producing xylenes may take place over a non-selective catalyst. Examples of non-selective catalysts include large pore zeolites, such as zeolite X and zeolite Y, or amorphous aluminosilicates. When toluene is disproportionated over a large pore size zeolite, equilibrium zeolites may be produced.

A selective process for producing PX is a process which produces PX in preference to other xylene isomers (MX and OX). A selective process for producing PX may be produced, for example, by a catalytic process over a PX selective catalyst. Examples of PX selective catalysts include medium pore size zeolites, such as ZSM-5, modified with selectivating agents. Selectivating agents may neutralize surface catalytic sites or narrow the pores of the catalyst. Examples of PX selective catalysts and selectivating agents are provided by in U.S. Pat. Nos. 5,365,004 and 4,088,706 and International Publication No. WO 2013/330093.

Circulating bulk fluid is the fluid (i.e., liquid) which flows in a continuous manner through a simulated moving bed adsorption apparatus. The concentration of compounds in this circulating bulk fluid changes as this fluid flows through the apparatus due to, inter alia, adsorption and desorption of xylenes, EB and desorbent, withdrawal of fluids in extract and reformate streams, and introduction of fluids through feed, desorbent and flush streams.

A liquid distribution device is one which distributes the flow of stream into and out of a simulated moving bed adsorptive separation device. A liquid distribution device may comprise a rotary valve or a system of other types of valves.

A rotary valve device is a device comprising at least one rotary valve. The rotary valve device may comprise various control and accessory means, such as inlet lines, outlet lines and valves associated therewith.

A simulated moving bed adsorption apparatus is an apparatus including beds of adsorbent stacked in at least one column.

A simulated countercurrent absorptive separation is a separation which takes place in a simulated moving bed adsorption apparatus.

An adsorbent column is an apparatus having adsorbent beds stacked therein.

An adsorbent bed chamber is a chamber in an adsorption apparatus containing a bed of adsorbent (i.e., adsorbent bed).

An adsorbent bed is a bed of adsorbent contained within an adsorbent bed chamber. An adsorbent column can include multiple adsorbent beds. An adsorbent apparatus can have one or more adsorbent columns. Any fluid in an adsorbent bed chamber, whether or not adsorbed on an adsorbent, is considered to be part of the bed. Accordingly, when fluid is introduced into or withdrawn from an adsorbent bed chamber, the fluid is considered as being introduced or withdrawn, into or from the bed itself.

An adsorbent is a solid material, which selectively adsorbs at least one $C_8$ aromatic in preference to other $C_8$ aromatics. In a simulated moving bed apparatus, examples of adsorbents include charcoal, ion-exchange resins, silica gel, activated carbon, zeolitic material, and the like. Examples of adsorbents for separating PX from other $C_8$ aromatics are described in U.S. Pat. No. 3,761,533. An example of an adsorbent for separating EB from MX and OX is a titanosilicate adsorbent, as described in U.S. Pat. Nos. 6,369,287; 5,244,650; 5,001,591; and 4,853,202.

Adsorbent selectivity is the tendency of an adsorbent to adsorb a particular compound from a mixture of compounds. In a PX separation process, the adsorbent will adsorb PX at a faster rate than other $C_8$ aromatics. The adsorbent may also adsorb EB at a faster rate than either MX or OX.

A desorbent is a liquid which displaces $C_8$ aromatics from adsorbent. The desorbent may be equally or slightly less preferentially adsorbed on the adsorbent than PX. The adsorbent can preferentially have a greater selectivity for the desorbent than $C_8$ aromatics. The desorbent may preferentially have a boiling point significantly different than the boiling points of $C_8$ aromatics, such that the desorbent may be separated from $C_8$ aromatics by distillation. Typical examples of a desorbent for a PX separation process include but are not limited to toluene or paradiethylbenzene (PDEB).

A line is a pipe or system of pipes for conveying a fluid.

A membrane separator is a unit that separates materials using a membrane based on, e.g., molecular polarity. Aromatics being more soluble in membrane material absorb in the membrane and diffuse to the permate side. Non-aromatics being less/non soluble remains on the feed side and are separated as rententate stream.

A number of abbreviations are used herein. PX stands for paraxylene. MX stands for MX. OX stands for OX. EB stands for ethylbenzene. pDEB stands for paradiethylbenzene. TOL stands for toluene. NA stands for non-aromatics such as paraffins, iso-paraffins, or naphthenes, which may be introduced into an adsorption apparatus as a feed impurity, especially when the feed comprises $C_8$ aromatics obtained from a reforming process. SMB stands for simulated moving bed.

Process/System of This Disclosure

According to embodiments of this disclosure, a process for separating PX from a mixture of PX, MX, OX, and EB comprises the steps of:

(i) processing a feed stream, comprising the mixture, and a desorbent supply stream, comprising desorbent, in a simulated moving bed adsorption apparatus to produce an extract stream comprising desorbent enriched in PX and a raffinate stream comprising desorbent lean in PX;

(ii) fractionating the extract stream to produce a first desorbent-rich stream and a PX-rich stream;

(iii) fractionating the raffinate stream to produce a second desorbent-rich stream and a mixed-$C_8$-aromatic-rich stream;

(iv) introducing a supply stream comprising at least a portion of one or both of the first desorbent-rich stream, the second desorbent-rich stream, or a combination thereof to a membrane separator to produce a permeate stream and a retentate stream, wherein the retentate stream is rich in non-aromatics relative to the permeate stream;

(v) supplying the permeate stream and any remaining portion(s) of the first desorbent-rich stream, the second desorbent-rich stream, or the combination thereof, to the desorbent stream to the simulated moving bed adsorption apparatus; and (vi) purging the retentate stream from the process.

According to embodiments, a system for separating PX from a mixture of PX, MX, OX, and EB comprises:

(i) a simulated moving bed adsorption apparatus to process a feed stream, comprising the mixture, and a desorbent supply stream, comprising desorbent, to produce an extract stream comprising desorbent enriched in PX and a raffinate stream comprising desorbent lean in PX;

(ii) an extract fractionation tower to fractionate the extract stream to produce a first desorbent-rich stream and a PX-rich product stream;

(iii) a raffinate fractionation tower to fractionate the raffinate stream to produce a second desorbent-rich stream and a mixed-$C_8$-aromatic-rich product stream;

(iv) a membrane separator to produce a permeate stream and a retentate stream, wherein the retentate stream is rich in non-aromatics relative to the permeate stream;

(v) a supply line to supply a supply stream comprising at least a portion of one or both of the first desorbent-rich stream, the second desorbent-rich stream, or a combination thereof, to the membrane separator;

(vi) a return line to return the permeate stream and any remaining portion(s) of the first desorbent-rich stream, the second desorbent-rich stream, or the combination thereof, to the desorbent stream to the simulated moving bed adsorption apparatus; and (vii) a purge line to purge the retentate stream from the system.

In any embodiment, the desorbent can comprise toluene. The desorbent supply stream preferably comprises at least 90 percent by weight toluene. For the purposes of simplicity and clarity, the following discussion may refer to the desorbent as toluene by way of example and not limitation.

In any embodiment, the first and second desorbent-rich streams from the fractionation towers can comprise different levels of non-aromatics. The membrane separator supply stream preferably comprises the one of the first and second desorbent-rich streams having the greater level of non-aromatics, i.e., the first desorbent-rich stream when it has a higher level of non-aromatics than the second desorbent-rich stream, and the second desorbent-rich stream when it has the higher level of non-aromatics.

In any embodiment, the membrane separator supply stream can comprise from 0.5 to 50 weight percent of a total of first and second desorbent-rich streams, preferably from 1 to 20 weight percent of the total weight of the first and second desorbent-rich streams, and more preferably from 2 to 10 weight percent of the total weight of the first and second desorbent-rich streams.

Preferably, a weight ratio of the permeate stream to the retentate stream can be from 1 to 20, preferably from 1 to 10. Often, the retentate stream can comprise from 0.1 to 10 wt % non-aromatics, more preferably from 0.2 to 5 wt % non-aromatics, based on the weight of the retentate stream. A weight ratio of the feed stream to the SMB to the desorbent supply stream to the SMB is preferably from 0.05 to 5, more preferably from 0.1 to 2, even more preferably from 0.4 to 2, and even more preferably from 0.67 to 1.5.

In any embodiment, the membrane separator can comprise a polyimide membrane, e.g., treated with a conditioning agent comprising a lubricating oil, or the membrane separator can comprise a liquid membrane, preferably a supported liquid membrane.

Preferably, a total mass flow of desorbent in the feed stream to the SMB and any other makeup desorbent stream matches a total mass flow of desorbent in the retentate stream and any other purge stream.

Steps (iv)-(vi) preferably improve PX product quality by reducing non-aromatics in the PX-rich product stream. If desired, operation of the simulated moving bed adsorption apparatus can be modulated to increase MX, OX, and/or EB in the extract stream up to an amount offsetting the reduction of non-aromatics in the PX-rich product stream, preferably wherein the modulation increases the quantity of the PX-rich product stream relative to the desorbent stream, and more preferably wherein the modulation further comprises reducing a quantity of the desorbent stream. For example, operation of the extract fractionation tower can be modulated for energy conservation by increasing a toluene content in the PX-rich product stream up to an amount offsetting the reduction of non-aromatics in the PX-rich product stream.

In any embodiment, the extract stream can comprise at least 99 weight percent of PX, preferably at least 99.7 weight percent of PX, based on the total amount of xylenes and EB present in the extract stream.

C9+ aromatics in the PX-rich product stream from the extract column preferably comprise no more than 0.5 weight percent of the PX-rich product stream, preferably no more than 0.3 weight percent of the PX-rich product stream, and more preferably no more than 0.1 weight percent of the PX-rich product stream. Non-aromatics in the PX-rich product stream from the extract column preferably comprise no more than 0.5 weight percent of the PX-rich product stream, preferably no more than 0.3 weight percent of the PX-rich product stream, and more preferably no more than 0.1 weight percent of the PX-rich product stream.

In any embodiment, the feed stream comprises equilibrium PX, preferably comprising at least 20 weight percent PX based on the total C8 aromatics content of the feed stream. Preferably, the feed stream comprises enhanced PX, preferably comprising at least 75 weight percent PX based on the total C8 aromatics content of the feed stream.

FIG. 2

Figure 2:
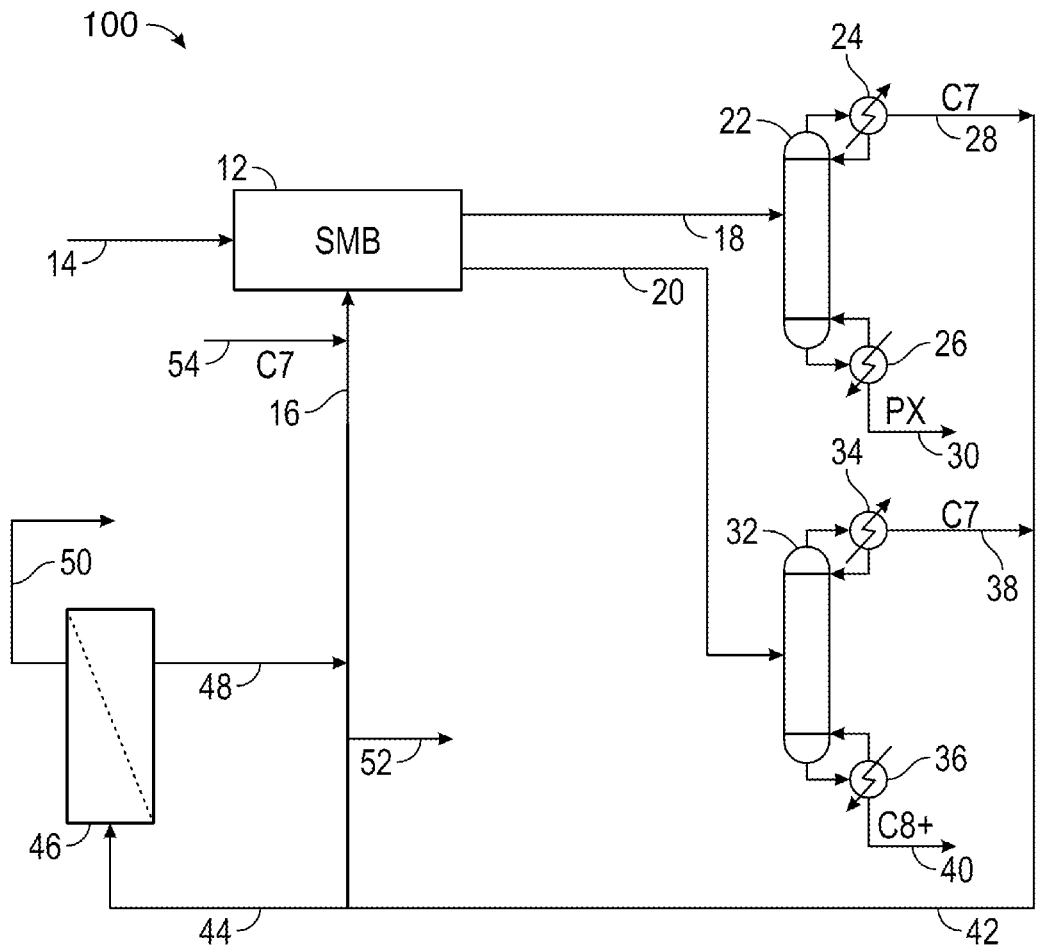
FIG. 2 is a schematic flow diagram of a simulated moving bed adsorptive separation process and system with combined desorbent stream membrane separation according to some embodiments of this disclosure.

FIG. 2 illustrates a process or system 100 having an SMB adsorption apparatus 12. The SMB 12 is particularly useful for separating one $C_8$ aromatic, such as PX, from a mixture of $C_8$ aromatics, such as a mixture of PX, MX, OX, and EB. The feed stream 14 can comprise equilibrium PX, enhanced PX, or a mixture or combination of equilibrium PX and/or enhanced PX. Where the feed stream comprises a combination of equilibrium PX and/or enhanced PX, the feed stream 14 may be divided for introduction at different places in the SMB 12. A feed stream or line 14 supplies the feed mix and a desorbent supply stream or line 16 supplies the desorbent, e.g., toluene, to the SMB 12. The feed stream 14 may optionally contain a mirror amount, e.g., less than 10 weight percent, of toluene or other desorbent. The SMB 12 produces an extract in stream or line 18, and a raffinate in stream or line 20. The extract 18 and raffinate 20 both comprise desorbent, and the extract 18 is enriched in PX relative to the raffinate 20.

Extract 18 is fractionated in extract column 22, which may be provided with an overhead condenser 24 and a reboiler 26. A first desorbent stream 28 is obtained overhead, and a product stream 30, rich in PX, is obtained from the bottoms.

Raffinate 20 is fractionated in raffinate column 32, which may be provided with an overhead condenser 34 and a reboiler 36. A second desorbent stream 38 is obtained overhead, and a raffinate product stream 40, lean in PX and rich in MX, OX, EB, and/or C8+ hydrocarbons, is obtained from the bottoms.

The desorbent streams 28, 38 are combined in recycle stream or line 42, which supplies desorbent to desorbent stream or line 16 to the SMB 12 as mentioned above. Non-aromatics having a boiling point equal to or less than $C_8$ aromatics will be produced from the columns 22, 32 with the desorbent in streams or lines 28, 38. A line or stream 44 comprising all or a portion (sidestream) can be withdrawn from the recycle 42 and processed in membrane separator unit 46. Membrane unit 46 produces a permeate supplied to stream or line 48 and a retentate supplied to stream or line 50. The permeate 48 is lean in non-aromatics, which are preferentially recovered in the retentate 50, which is purged from the process or system 100. If desired, an upstream purge 52 can be taken from line or stream 42 or sidestream 44 and/or makeup desorbent supplied downstream via line or stream 54. All or part of the makeup desorbent may be supplied in the feed stream 14 as mentioned above.

FIG. 3

Figure 3:
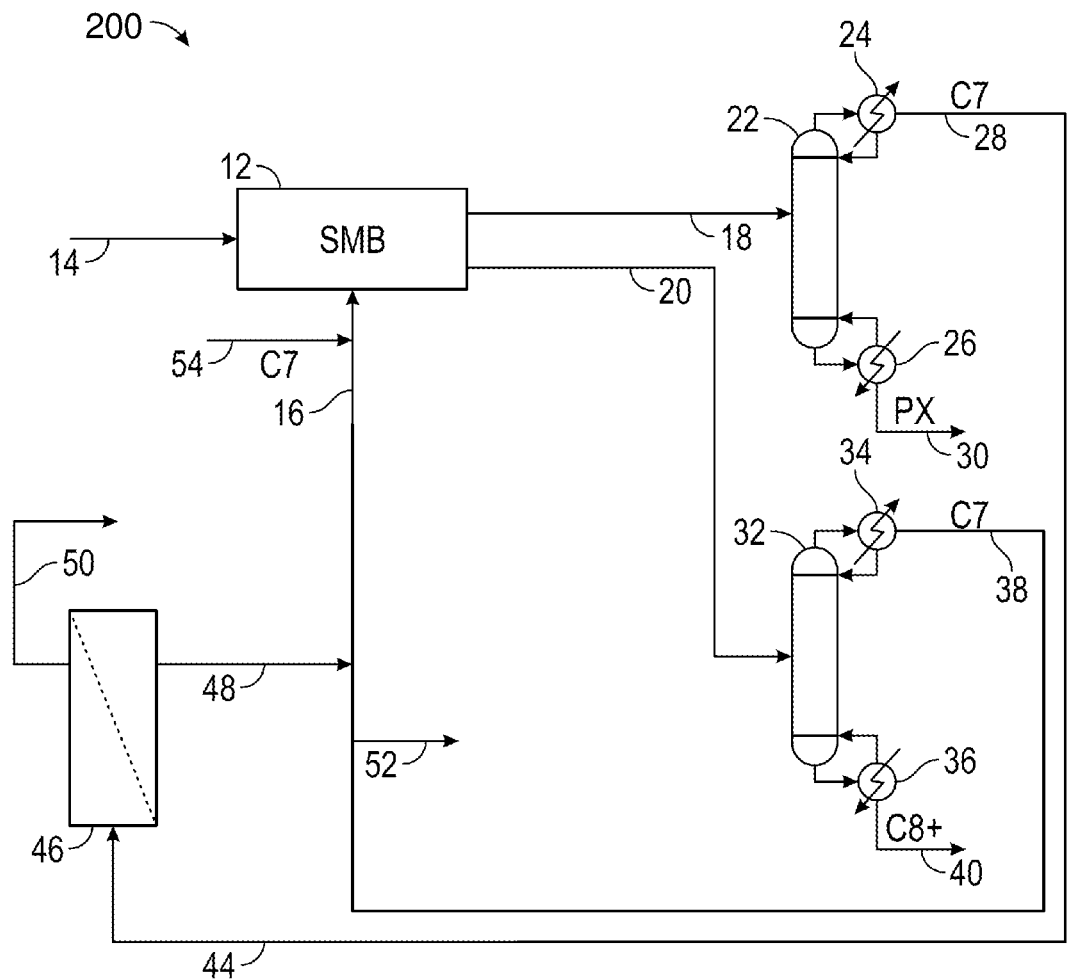
FIG. 3 is a schematic flow diagram of a simulated moving bed adsorptive separation process and system with membrane separation of the extract column desorbent according to some embodiments of this disclosure.

FIG. 3 illustrates process or system 200 having an SMB adsorption apparatus 12 as described in connection with FIG. 2. A feed stream or line 14 supplies the feed mix, optionally containing some desorbent, e.g., toluene, and a desorbent supply stream or line 16 supplies the desorbent to the SMB 12. The SMB 12 produces an extract in stream or line 18, and a raffinate in stream or line 20. The extract 18 and raffinate 20 both comprise desorbent, and the extract 18 is enriched in PX relative to the raffinate 20.

As described in connection with FIG. 2, in FIG. 3 extract 18 is fractionated in extract column 22, which may be provided with an overhead condenser 24 and a reboiler 26. A first desorbent stream 28 is obtained overhead, and a product stream 30, rich in PX, is obtained from the bottoms. Raffinate 20 is fractionated in raffinate column 32, which may be provided with an overhead condenser 34 and a reboiler 36. A second desorbent stream 38 is obtained overhead, and a raffinate product stream 40, lean in PX and rich in MX, OX, EB, and/or C8+ hydrocarbons is obtained from the bottoms.

In FIG. 3, the first desorbent stream 28 may contain a higher non-aromatics content than second desorbent stream 38, and in this case all or part of the stream 28 can be processed in membrane separator unit 46. Membrane unit 46 produces a permeate supplied to stream or line 48 and a retentate supplied to stream or line 50. The permeate 48 is lean in non-aromatics, which are preferentially recovered in the retentate 50, which is purged from the process or system 200. The permeate 48 is combined with second desorbent stream 38 and any added makeup desorbent 54, and supplied to desorbent supply 16 to the SMB 12. If desired, an upstream purge 52 can be taken from line or stream 28.

FIG. 4

Figure 4:
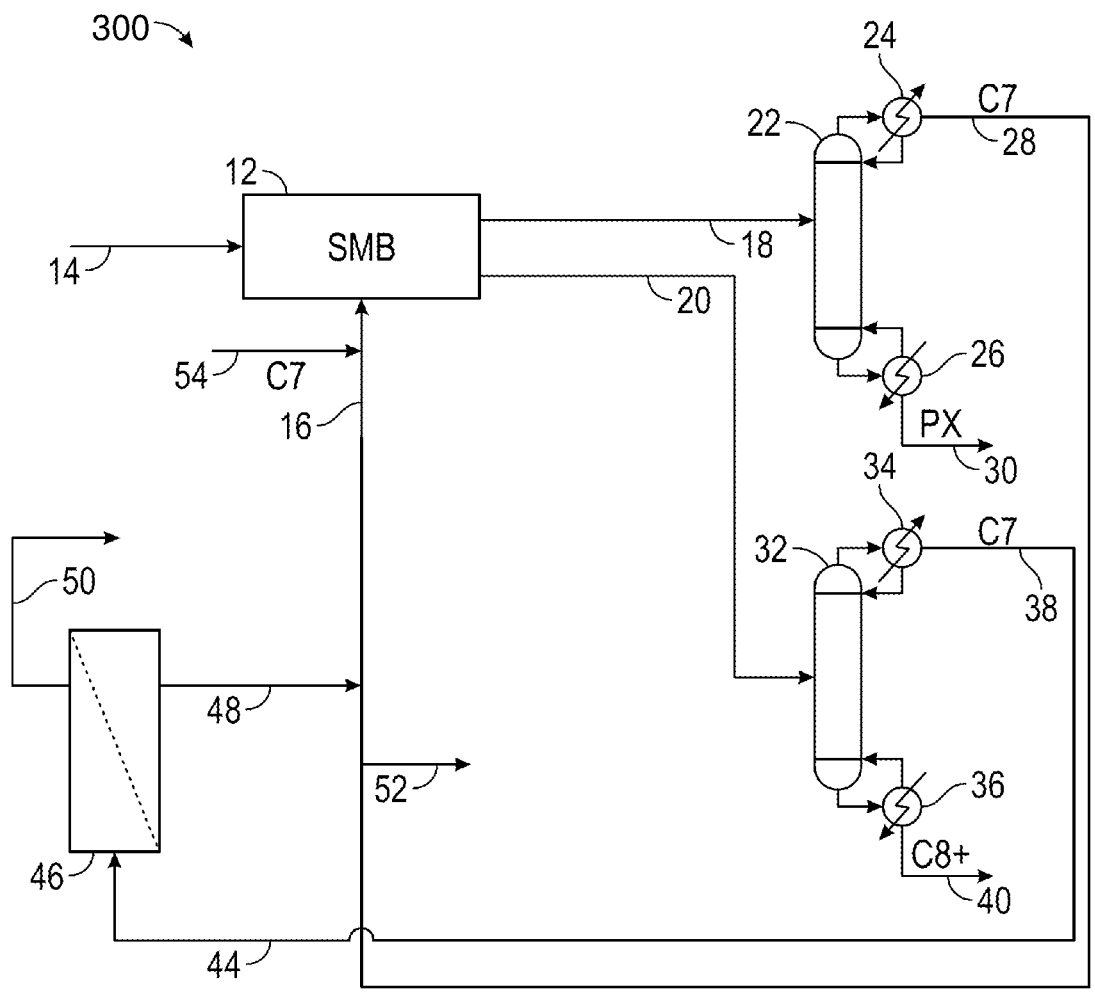
FIG. 4 is a schematic flow diagram of a simulated moving bed adsorptive separation process and system with membrane separation of the raffinate column desorbent according to some embodiments of this disclosure.

FIG. 4 illustrates process or system 300 having an SMB adsorption apparatus 12 as described in connection with FIG. 2. A feed stream or line 14 supplies the feed mix, optionally containing some desorbent, e.g., toluene, and a desorbent supply stream or line 16 supplies the desorbent to the SMB 12. The SMB 12 produces an extract in stream or line 18, and a raffinate in stream or line 20. The extract 18 and raffinate 20 both comprise desorbent, and the extract 18 is enriched in PX relative to the raffinate 20.

As described in connection with FIG. 2, in FIG. 4 extract 18 is fractionated in extract column 22, which may be provided with an overhead condenser 24 and a reboiler 26. A first desorbent stream 28 is obtained overhead, and a product stream 30, rich in PX, is obtained from the bottoms. Raffinate 20 is fractionated in raffinate column 32, which may be provided with an overhead condenser 34 and a reboiler 36. A second desorbent stream 38 is obtained overhead, and a raffinate product stream 40, lean in PX and rich in MX, OX, EB, and/or C8+ hydrocarbons is obtained from the bottoms.

In FIG. 4, the second desorbent stream 38 may contain a higher non-aromatics content than first desorbent stream 28, and in this case all or part of the stream 38 can be processed in membrane separator unit 46. Membrane unit 46 produces a permeate supplied to stream or line 48 and a retentate supplied to stream or line 50. The permeate 48 is lean in non-aromatics, which are preferentially recovered in the retentate 50, which is purged from the process or system 300. The permeate 48 is combined with first desorbent stream 28 and any added makeup desorbent 54, and supplied to desorbent supply 16 to the SMB 12. If desired, an upstream purge 52 can be taken from line or stream 38.

Membrane Separators

A membrane separator useful in the processes according to the various aspects of this disclosure can comprise a vessel having a first volume, a second volume, and a membrane between the first volume and the second volume. The first volume is separate from the second volume by the membrane. An admixture stream comprising a first component and a second component having a lower polarity than the first component is supplied into the first volume. The membrane is selected to have a polarity such that it is more permeable to the first component than to the second component. Thus, on contacting the admixture stream, the membrane preferentially permits the first component to permeate through to enter into the second volume, from which a permeate stream rich in the first component and depleted in the second component relative to the admixture stream exits. A retentate stream exiting the first volume becomes depleted in the first component and rich in the second component relative to the admixture stream. The permeation of component(s) through the membrane is preferentially facilitated by a pressure drop from the first volume to the second volume. Structure and operation of exemplary membrane separator are provided in FIG. 1 and described in greater detail below.

The membrane can be polymer-based. The term polymer includes, but is not limited to, homopolymers, copolymers, terpolymers, polymer blends, and the like. For example, suitable polymers for the membrane include, but are not limited to, polyesters, polyethers, polysulfones, polyimides, polyamides, polymers derived from bisphenol-A dianhydride, polyvinyl alcohols, polyacrylonitriles, polyurethanes, polyureas, polyacrylic acids, polyacrylates, elastomeric polymers such as polybutadiene, polyisoprenes, polyvinylpyridines, halogenated polymers, fluoroelastomers, polyvinyl halides, polysiloxanes, poly dimethyl siloxanes, a copolymer comprising at least one of the foregoing polymers, a blend comprising at least one of the foregoing polymers, an alloy comprising at least one of the foregoing polymers, or a combination comprising at least one of the foregoing polymers, copolymers, blends, or alloys. The polymers could be further physically or chemically rosslinked to increase chemical stability.

In various preferred embodiments, the membrane can be a polyimide-based membrane treated by a lubricating oil. In other embodiments, the membrane can comprise an ionic liquid carried by an organic or inorganic matrix material.

Description of exemplary membranes, membrane separators, and membrane separation processes useful in the processes of the aspects of this disclosure include, e.g., U.S. Pat. Nos. 4,571,444; 6,187,987; 6,180,008; and 7,642,393; and Zhang, Fan, "Selective Separation of Toluene/n-Heptane by Supported Ionic Liquid Membranes with [Bmim][BF4]," Chem. Eng. Technol. 2015, 38, No. 2, 355-361, the relevant contents in which are incorporated herein by reference.

FIG. 1 schematically illustrates the cross-sectional structure and operation of an exemplary membrane separator useful in embodiments of the processes of this disclosure comprising a vessel 101. Vessel 101 comprises an inner conduit and an outer jacket affixed to and surrounding the outer surface of the inner conduit. Vessel 101 comprises a first volume 103, a second volume 105, and a membrane 107 between volumes 103 and 105. Volume 103 is defined by the inner surface of a wall 115 of the inner conduit. Wall 115 comprises a perforated segment 109 through which fluid can freely pass. The membrane 107 is shown installed on the outer surface of wall 115 covering the perforated segment 109 in FIG. 1, although alternatively or additionally, it may be installed on the inner surface of wall 115. The second volume 105 is defined by the outer surface of wall 115, the outer surface of membrane 107, and the inner surface of the wall 111 of the outer jacket. During operation of the membrane separator, an admixture stream 117 (preferably in liquid phase) at a first pressure comprising a first component (e.g., aromatics) and a second component (e.g., non-aromatics) having a lower polarity than the first component is supplied into the first volume 103 through the inlet end of the inner conduit. The admixture stream then flows along the inner conduit, partly through the perforated segment 109 and then contacts the membrane 107. Due to a pressure drop from the first volume 103 to the second volume 105, a portion of the first component and optionally a portion of the second component pass through the membrane 107 to enter the second volume 105. Without intending to be bound by a particular theory, it is believed that because the first component has higher polarity than the second component, passage of the first component through the membrane 107 is favored over the second component, resulting in the formation of a fluid in the second volume 105 rich in the first component and depleted in the second component relative to admixture stream 117. A portion of the fluid in the second volume 105 exits an outlet 113 as a permeate stream 121. The retentate stream 119 exiting from the first volume 103, shown in FIG. 1 at the outlet end of the inner conduit, is depleted in the first component and rich in the second component relative to the admixture stream 117.

According to embodiments of this disclosure, the permeate 48 shown in the various drawings is preferably larger than the retentate 50, e.g., at a weight ratio of from greater than 1 up to 20, more preferably from 1 to 10, e.g., 80% permeate and 20% retentate (4:1). At the same time, the non-aromatics are concentrated in the retentate 50 such that more than 50% of the non-aromatics from the sidestream 44 are passed with the retentate 50, preferably more than 70%, and more preferably more than 85%, e.g., 90% of the non-aromatics can be passed to the retentate 50. In this scenario, the retentate 50 has a higher concentration of the non-aromatics than the desorbent 16, but the non-aromatics can be a minor component of the retentate, e.g., from 0.1 to 10 wt % non-aromatics, e.g., from 0.2 to 5 wt % non-aromatics.

Adsorbents and Desorbents

When PX is separated from a mixture of $C_8$ aromatics, the adsorbent may be, for example, one of those that are described in U.S. Pat. Nos. 3,626,020 and 3,878,127. Such an adsorbent may be an X zeolite that is exchanged with barium and hydrated or a Y zeolite that is exchanged with potassium and barium. The desorbent for this PX separation process may comprise pDEB, TOL, and/or tetralin. A tetralin desorbent is described in U.S. Pat. No. 8,283,274.

When EB is separated from a mixture of $C_8$ aromatics, e.g., from which PX has been separated, the adsorbent may be the same as or different from the adsorbent used to separate PX from a mixture of $C_8$ aromatics. Such an adsorbent may contain at least one element that is selected from the group of elements K, Rb, Cs, Ba, Ca, and Sr and optionally water. Examples of such EB selective adsorbents are described in, for example, U.S. Pat. Nos. 5,453,560; 4,613,725; 4,108,915; 4,079,094; and 3,943,182. Another type of an adsorbent for separating EB from a mixture of $C_8$ aromatics may comprise a titanosilicate. Titanosilicate-containing adsorbents may have a pore opening on the order of 8 Å. Such titanosilicate-containing adsorbents are described in U.S. Pat. Nos. 5,244,650; 5,011,591; and 4,853,202. When a titanosilicate-containing adsorbent is used to separate EB from a mixture of $C_8$ aromatics, the desorbent may be pDEB, TOL, or a mixture thereof.

When MX or OX is separated from a mixture of $C_8$ aromatics, an adsorbent selective for either MX or OX may be used, such as a Metal Organic Frameworks (MOF). MOFs have metal ions or clusters of metal ions and organic molecules called linkers. Metal organic framework materials are described in U.S. Pat. Nos. 5,648,508 and 7,662,746, and U.S. Patent Publication No. 2009/0305040. The MOF adsorbent may be used in a SMB unit, and para-diethylbenzene, TOL, or 1,4-di-n-isopropylbenzene may be used as a desorbent.

Suitable MOF adsorbents for separating OX or MX from mixtures of $C_8$ aromatics may be determined by testing MOFs on their ability to sorb OX or MX and the ability of desorbents to desorb the OX or MX. Examples of suitable OX selective MOFs are Cr-MIL-101, which is described in U.S. Pat. No. 8,704,031, and MIL-47 (V), which is described in Angew. Chem. Int. Ed. 2002; Phys. Chem. Phys., 2008, 10, 2979 and U.S. Pat. No. 9,102,609. When MIL-47 (V) is used as an OX selective adsorbent, the desorbent may be n-heptane.

When PX is separated from a mixture of $C_8$ aromatics, the extract stream withdrawn may preferably comprise at least 99 weight percent of PX, more preferably at least 99.7 weight percent of PX, based on the total amount of xylenes and EB present in the extract stream. In any embodiment, the C9+ aromatics in the PX-rich product stream from the extract column can comprise no more than 0.5 weight percent of the PX-rich product stream, preferably no more than 0.3 weight percent of the PX-rich product stream, and more preferably no more than 0.1 weight percent of the PX-rich product stream. In any embodiment, the non-aromatics in the PX-rich product stream from the extract column comprise no more than 0.5 weight percent of the PX-rich product stream, preferably no more than 0.3 weight percent of the PX-rich product stream, and more preferably no more than 0.1 weight percent of the PX-rich product stream. As described above, the extract stream is separated by distillation downstream to provide a purified PX product and a stream rich in desorbent, which is recycled to for re-use in the SMB adsorptive separation process.

Embodiments

Other non-limiting aspects and/or embodiments of the present disclosure can include:

E1. A process for separating paraxylene (PX) from a mixture of PX, metaxylene (MX), orthoxylene (OX), and ethylbenzene (EB), comprising the steps of:
  (i) processing a feed stream, comprising the mixture, and a desorbent supply stream, comprising desorbent, in a simulated moving bed adsorption apparatus to produce an extract stream comprising desorbent enriched in PX and a raffinate stream comprising desorbent lean in PX;
  (ii) fractionating the extract stream to produce a first desorbent-rich stream and a PX-rich stream;
  (iii) fractionating the raffinate stream to produce a second desorbent-rich stream and a mixed-$C_8$-aromatic-rich stream;
  (iv) introducing a supply stream comprising at least a portion of one or both of the first desorbent-rich stream, the second desorbent-rich stream, or a combination thereof to a membrane separator to produce a permeate stream and a retentate stream, wherein the retentate stream is rich in non-aromatics relative to the permeate stream;
  (v) supplying the permeate stream and any remaining portion(s) of the first desorbent-rich stream, the second desorbent-rich stream, or the combination thereof, to the desorbent stream to the simulated moving bed adsorption apparatus; and
  (vi) purging the retentate stream from the process.

E2. The process of embodiment E1, wherein the desorbent comprises toluene, preferably wherein the desorbent supply stream comprises at least 90 percent by weight toluene.

E3. The process of embodiment E1 or E2, wherein the first and second desorbent-rich streams comprise different levels of non-aromatics, and wherein the membrane separator supply stream comprises the one of the first and second desorbent-rich streams having the greater level of non-aromatics.

E4. The process of any of E1 to E3, wherein the first desorbent-rich stream has a higher level of non-aromatics than the second desorbent-rich stream.

E5. The process of any of E1 to E3, wherein the second desorbent-rich stream has a higher level of non-aromatics than the first desorbent-rich stream.

E6. The process of any preceding embodiment, wherein the membrane separator supply stream comprises from 0.5 to 50 weight percent of a total of first and second desorbent-rich streams, preferably from 1 to 20 weight percent of the total weight of the first and second desorbent-rich streams, more preferably from 2 to 10 weight percent of the total weight of the first and second desorbent-rich streams.

E7. The process of any preceding embodiment, wherein a weight ratio of the permeate stream to the retentate stream is from 1 to 20, preferably from 1 to 10, preferably wherein the retentate stream comprises from 0.1 to 10 wt % non-aromatics, more preferably from 0.2 to 5 wt % non-aromatics, based on the weight of the retentate stream.

E8. The process of any preceding embodiment, wherein a weight ratio of the feed stream to the desorbent stream is from 0.05 to 5, preferably from 0.1 to 2, more preferably from 0.4 to 2, and even more preferably from 0.67 to 1.5.

E9. The process of any preceding embodiment, wherein the membrane separator comprises a polyimide membrane treated with a conditioning agent comprising a lubricating oil.

E10. The process of any of embodiments E1-E8, wherein the membrane separator comprises a liquid membrane, preferably a supported liquid membrane.

E11. The process of any preceding embodiment, wherein a total mass flow of desorbent in the feed stream and any makeup desorbent stream matches a total mass flow of desorbent in the retentate stream and any other purge stream.

E12. The process of any preceding embodiment, wherein steps (iv)-(vi) improve PX product quality by reducing non-aromatics in the PX-rich product stream.

E13. The process of embodiment E12, wherein operation of the simulated moving bed adsorption apparatus is modulated to increase MX, OX, and/or EB in the extract stream up to an amount offsetting the reduction of non-aromatics in the PX-rich product stream, preferably wherein the modulation increases the quantity of the PX-rich product stream relative to the desorbent stream, and more preferably wherein the modulation further comprises reducing a quantity of the desorbent stream.

E14. The process of embodiment E12 or E13, further comprising modulating operation of the extract fractionation tower for energy conservation by increasing a toluene content in the PX-rich product stream up to an amount offsetting the reduction of non-aromatics in the PX-rich product stream.

E15. The process of any preceding embodiment, wherein the extract stream comprises at least 99 weight percent of PX, more preferably at least 99.7 weight percent of PX, based on the total amount of xylenes and EB present in the extract stream.

E16. The process of any preceding embodiment, wherein $C_9+$ aromatics in the PX-rich product stream from the extract column comprise no more than 0.5 weight percent of the PX-rich product stream, preferably no more than 0.3 weight percent of the PX-rich product stream, and more preferably no more than 0.1 weight percent of the PX-rich product stream.

E17. The process of any preceding embodiment, wherein non-aromatics in the PX-rich product stream from the extract column comprise no more than 0.5 weight percent of the PX-rich product stream, preferably no more than 0.3 weight percent of the PX-rich product stream, and more preferably no more than 0.1 weight percent of the PX-rich product stream.

E18. The process of any preceding embodiment, wherein the feed stream comprises equilibrium PX, preferably comprising at least 20 weight percent PX based on the total C8 aromatics content of the feed stream.

E19. The process of any preceding embodiment, wherein the feed stream comprises enhanced PX, preferably comprising at least 75 weight percent PX based on the total C8 aromatics content of the feed stream.

E20. A system for separating paraxylene (PX) from a mixture of PX, metaxylene (MX), orthoxylene (OX), and ethylbenzene (EB), comprising:
(i) a simulated moving bed adsorption apparatus to process a feed stream, comprising the mixture, and a desorbent supply stream, comprising desorbent, to produce an extract stream comprising desorbent enriched in PX and a raffinate stream comprising desorbent lean in PX;
(ii) an extract fractionation tower to fractionate the extract stream to produce a first desorbent-rich stream and a PX-rich product stream;
(iii) a raffinate fractionation tower to fractionate the raffinate stream to produce a second desorbent-rich stream and a mixed-C8-aromatic-rich product stream;
(iv) a membrane separator to produce a permeate stream and a retentate stream, wherein the retentate stream is rich in non-aromatics relative to the permeate stream;
(v) a supply line to supply a supply stream comprising at least a portion of one or both of the first desorbent-rich stream, the second desorbent-rich stream, or a combination thereof, to the membrane separator;
(vi) a return line to return the permeate stream and any remaining portion(s) of the first desorbent-rich stream, the second desorbent-rich stream, or the combination thereof, to the desorbent stream to the simulated moving bed adsorption apparatus; and
(vii) a purge line to purge the retentate stream from the system.

E21. The system of embodiment E20, wherein the desorbent comprises toluene, preferably wherein the desorbent supply stream comprises at least 90 percent by weight toluene.

E22. The system of embodiment E20 or E21, wherein the first and second desorbent-rich streams comprise different levels of non-aromatics, and wherein the membrane separator supply stream comprises the one of the first and second desorbent-rich streams having the greater level of non-aromatics.

E23. The system of any of embodiments E20-E22, wherein the first desorbent-rich stream has a higher level of non-aromatics than the second desorbent-rich stream.

E24. The system of any of embodiments E20-E22, wherein the second desorbent-rich stream has a higher level of non-aromatics than the first desorbent-rich stream.

E25. The system of any of embodiments E20-E24, wherein the membrane separator supply stream comprises from 0.5 to 50 weight percent of a total of the first and second desorbent streams, preferably from 1 to 20 weight percent of the total weight of the first and second desorbent streams, more preferably from 2 to 10 weight percent of the total weight of the first and second desorbent streams.

E26. The system of any of embodiments E20-E25, wherein a weight ratio of the permeate stream to the retentate stream is from 1 to 20, preferably from 1 to 10, preferably wherein the retentate stream comprises from 0.1 to 10 wt % non-aromatics, more preferably from 0.2 to 5 wt % non-aromatics, based on the weight of the retentate stream.

E27. The system of any of embodiments E20-E26, wherein a weight ratio of the feed stream to the desorbent stream is from 0.05 to 5, preferably from 0.1 to 2, more preferably from 0.4 to 2, and even more preferably from 0.67 to 1.5.

E28. The system of any of embodiments E20-E27, wherein the membrane separator comprises a polyimide membrane treated with a conditioning agent comprising a lubricating oil.

E29. The system of any of embodiments E20-E27, wherein the membrane separator comprises a liquid membrane, preferably a supported liquid membrane.

E30. The system of any of embodiments E20-E29, wherein a total mass flow of desorbent in the feed stream and any makeup desorbent stream matches a total mass flow of desorbent in the retentate stream and any other purge stream.

E31. The system of any of embodiments E20-E30, wherein the membrane separator improves PX product quality by reducing non-aromatics in the PX-rich product stream.

E32. The system of embodiment E31, wherein operation of the simulated moving bed adsorption apparatus is modulated to increase MX, OX, and/or EB in the extract stream up to an amount offsetting the reduction of non-aromatics in the PX-rich product stream.

E33. The system of embodiment E32, wherein the modulation increases the quantity of the PX-rich product stream relative to the desorbent stream, preferably wherein the modulation further comprises reducing a quantity of the desorbent stream.

E34. The system of any of embodiments E20-E33, wherein operation of the extract fractionation tower is modulated for energy conservation by increasing a toluene content in the PX-rich product stream up to an amount offsetting the reduction of non-aromatics in the PX-rich product stream.

E35. The system of any of embodiments E20-E34, wherein the extract stream comprises at least 99 weight percent of PX, more preferably at least 99.7 weight percent of PX, based on the total amount of xylenes and EB present in the extract stream.

E36. The system of any of embodiments E20-E35, wherein $C_9+$ aromatics in the PX-rich product stream from the extract column comprise no more than 0.5 weight percent of the PX-rich product stream, preferably no more than 0.3 weight percent of the PX-rich product stream, and more preferably no more than 0.1 weight percent of the PX-rich product stream.

E37. The system of any of embodiments E20-E36, wherein non-aromatics in the PX-rich product stream from the extract column comprise no more than 0.5 weight percent of the PX-rich product stream, preferably no more than 0.3 weight percent of the PX-rich product stream, and more preferably no more than 0.1 weight percent of the PX-rich product stream.

E38. The system of any of embodiments E20-E37, wherein the feed stream comprises equilibrium PX, preferably comprising at least 20 weight percent PX based on the total C8 aromatics content of the feed stream.

E39. The system of any of embodiments E20-E38, wherein the feed stream comprises enhanced PX, preferably comprising at least 75 weight percent PX based on the total C8 aromatics content of the feed stream.

This disclosure is further illustrated by the following non-limiting example.

EXAMPLE

In this example, a process/system illustrated in FIG. 2 is simulated. The feed 14 comprises a mixed xylenes stream at n KTA containing minor amounts of toluene and non-aromatics. The toluene desorbent 16 is supplied to the SMB 12 at 2.3 n KTA. The PX product stream 30 is obtained at 0.22n KTA, and the PX-depleted mixed xylene stream 40 is obtained at 0.76n KTA. The toluene is recovered in line 42 from the towers 22, 32 at a rate of 2.3n KTA. Without the membrane separator 44 and at a purge rate of 0.024n KTA via line 52, the toluene desorbent stream 16 has a non-aromatics content of 0.8 wt %, and the PX product contains 0.033 wt % non-aromatics. Then the system is retrofitted with the membrane separator 46 as shown in the FIG. 2 to receive 5.5% of the circulating desorbent from line 42 such that 90% of the feed non-aromatics in sidestream 44 are contained in the retentate 50, and the permeate 48 contains 80% of the feed toluene from sidestream 44. Thus, the retentate 50 is purged from the system 100 at a rate of 0.024n KTA. Following the retrofit, the toluene desorbent stream 16 has a non-aromatics content of 0.13 wt %, and the PX product 30 contains just 0.006 wt % (6 ppmwt) non-aromatics. As variations, it is now possible to increase the rate of feed 14, reduce the desorbent feed 16, and/or reduce the energy used to operate the columns 22, 32, while meeting the same overall product purity specifications prior to the retrofit.

While particular embodiments have been described and illustrated herein, those of ordinary skill in the art will appreciate that the invention lends itself to variations not necessarily illustrated herein. For this reason, then, reference should be made solely to the appended claims for purposes of determining the true scope of this disclosure.

What is claimed is:

1. A process for separating paraxylene (PX) from a mixture of PX, metaxylene (MX), orthoxylene (OX), and ethylbenzene (EB), comprising the steps of:
   (i) processing a feed stream, comprising the mixture, and a desorbent supply stream, comprising desorbent, in a simulated moving bed adsorption apparatus to produce an extract stream comprising desorbent enriched in PX and a raffinate stream comprising desorbent lean in PX;
   (ii) fractionating the extract stream to produce a first desorbent-rich stream and a PX-rich stream;
   (iii) fractionating the raffinate stream to produce a second desorbent-rich stream and a mixed-C8-aromatic-rich stream;
   (iv) introducing a supply stream comprising at least a portion of one or both of the first desorbent-rich stream, the second desorbent-rich stream, or a combination thereof to a membrane separator to produce a permeate stream and a retentate stream, wherein the retentate stream is rich in non-aromatics relative to the permeate stream;
   (v) supplying the permeate stream and any remaining portion(s) of the first desorbent-rich stream, the second desorbent-rich stream, or the combination thereof, to the desorbent supply stream to the simulated moving bed adsorption apparatus; and
   (vi) purging the retentate stream from the process.

2. The process of claim 1, wherein the desorbent comprises toluene, preferably wherein the desorbent stream comprises at least 90 percent by weight toluene, based on the total weight of the desorbent stream.

3. The process of claim 1, wherein the first and second desorbent-rich streams comprise different levels of non-aromatics, and wherein the membrane separator supply stream comprises the one of the first and second desorbent-rich streams having the greater level of non-aromatics.

4. The process of claim 1, wherein the membrane separator supply stream constitutes from 0.5 to 50 weight percent of the total weight of the first and second desorbent-rich streams.

5. The process of claim 4, wherein the membrane separator supply stream constitutes from 1 to 20 weight percent of the total weight of the first and second desorbent-rich streams.

6. The process of claim 4, wherein the membrane separator supply stream constitutes from 2 to 10 weight percent of the total weight of the first and second desorbent-rich streams.

7. The process of claim 1, wherein the weight ratio of the permeate stream to the retentate stream is from 1 to 20.

8. The process of claim 7, wherein the weight ratio of the permeate stream to the retentate stream from 1 to 10.

9. The process of claim 1, wherein the retentate stream comprises from 0.1 to 10 wt % non-aromatics, based on the total weight of the retentate stream.

10. The process of claim 9, wherein the retentate stream comprises from 0.2 to 5 wt % non-aromatics, based on the total weight of the retentate stream.

11. The process of claim 1, wherein the weight ratio of the feed stream to the desorbent stream is from 0.05 to 5.

12. The process of claim 11, wherein the weight ratio of the feed stream to the desorbent stream is from 0.1 to 2.

13. The process of claim 11, wherein the weight ratio of the feed stream to the desorbent stream is from 0.4 to 2.

14. The process of claim 11, the weight ratio of the feed stream to the desorbent stream is from 0.67 to 1.5.

15. The process of claim 1, wherein the membrane separator comprises a polyimide membrane treated with a conditioning agent comprising a lubricating oil.

16. The process of claim 1, wherein the membrane separator comprises a liquid membrane, preferably a supported ionic liquid membrane.

17. The process of claim 1, wherein the total mass flow of desorbent in the feed stream and any makeup desorbent stream matches the total mass flow of desorbent in the retentate stream and any purge stream.

18. The process of claim 1, wherein steps (iv)-(vi) improve PX product quality by reducing non-aromatics in the PX-rich product stream.

19. The process of claim 18, wherein operation of the simulated moving bed adsorption apparatus is modulated to increase MX, OX, and/or EB in the extract stream up to an amount offsetting the reduction of non-aromatics in the PX-rich product stream, preferably wherein the modulation increases the quantity of the PX-rich product stream relative to the desorbent stream, and more preferably wherein the modulation further comprises reducing a quantity of the desorbent stream.

20. The process of claim 18, further comprising modulating operation of the extract fractionation tower for energy conservation by increasing a toluene content in the PX-rich product stream up to an amount offsetting the reduction of non-aromatics in the PX-rich product stream.

21. A system for separating paraxylene (PX) from a mixture of PX, metaxylene (MX), orthoxylene (OX), and ethylbenzene (EB), comprising:
  (i) a simulated moving bed adsorption apparatus to process a feed stream, comprising the mixture, and a desorbent supply stream, comprising desorbent, to produce an extract stream comprising desorbent enriched in PX and a raffinate stream comprising desorbent lean in PX;
  (ii) an extract fractionation tower to fractionate the extract stream to produce a first desorbent-rich stream and a PX-rich product stream;
  (iii) a raffinate fractionation tower to fractionate the raffinate stream to produce a second desorbent-rich stream and a mixed-C8-aromatic-rich product stream;
  (iv) a membrane separator to produce a permeate stream and a retentate stream, wherein the retentate stream is rich in non-aromatics relative to the permeate stream;
  (v) a supply line to supply the desorbent supply stream to the membrane separator, wherein the desorbent supply stream comprises at least a portion of one or both of the first desorbent-rich stream, the second desorbent-rich stream, or the combination thereof;
  (vi) a return line to return the permeate stream and any remaining portion(s) of the first desorbent-rich stream, the second desorbent-rich stream, or the combination thereof, to the desorbent stream to the simulated moving bed adsorption apparatus; and
  (vii) a purge line to purge the retentate stream from the system.

22. The system of claim 21, wherein the desorbent comprises toluene, preferably wherein the desorbent stream comprises at least 90 percent by weight toluene.

23. The system of claim 21, wherein the first and second desorbent-rich streams comprise different levels of non-aromatics, and wherein the membrane separator supply stream comprises the one of the first and second desorbent-rich streams having the greater level of non-aromatics.

24. The system of claim 21, wherein the membrane separator comprises a polyimide membrane treated with a conditioning agent comprising a lubricating oil.

25. The system of claim 21, wherein the membrane separator comprises a liquid membrane, preferably a supported liquid membrane.

* * * * *